US008642266B2

(12) United States Patent
Bergtsson et al.

(10) Patent No.: US 8,642,266 B2
(45) Date of Patent: *Feb. 4, 2014

(54) SINGLE CELL MRNA QUANTIFICATION WITH REAL-TIME RT-PCR

(75) Inventors: Martin Bergtsson, Malmö (SE); Michael Kubista, Moelndal (SE); Anders Stahlberg, Molndal (SE); Linda Stroembom, Goeteborg (SE)

(73) Assignee: RocheDiagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/603,648

(22) Filed: Oct. 22, 2009

(65) Prior Publication Data

US 2010/0216194 A1      Aug. 26, 2010

Related U.S. Application Data

(63) Continuation of application No. PCT/EP2008/003451, filed on Apr. 29, 2008.

(30) Foreign Application Priority Data

May 3, 2007   (EP) ..................................... 07008961

(51) Int. Cl.
*C12Q 1/68* (2006.01)
*C12P 19/34* (2006.01)
*C07H 21/04* (2006.01)

(52) U.S. Cl.
USPC ........................ 435/6.12; 435/91.2; 536/24.33

(58) Field of Classification Search
USPC .......................... 435/6, 91.2, 91.21; 536/24.33
See application file for complete search history.

(56) References Cited

U.S. PATENT DOCUMENTS

| 5,637,687 | A  | * | 6/1997  | Wiggins ........................ 536/25.4 |
| 2002/0009794 | A1 |   | 1/2002  | Danenberg et al. |
| 2003/0170617 | A1 | * | 9/2003  | Pasloske ............... 435/5 |
| 2006/0286557 | A1 | * | 12/2006 | Basehore et al. ................. 435/6 |
| 2008/0003575 | A1 | * | 1/2008  | Michalik et al. .................. 435/6 |

FOREIGN PATENT DOCUMENTS

| EP | 1529841 A1 | 5/2004 |
| WO | WO 2004104181 A2 * | 12/2004 |
| WO | 2005/090984 A1 | 9/2005 |

OTHER PUBLICATIONS

Bengtsson, M et al. Gene expression profiling in single cells from the pancreatic islets of Langerhans reveals lognormal distribution of mRNA levels. Genome Research, vol. 15, pp. 1388-1392, 2005.*
Hartshorn C. et al. Rapid, single-tube method for quantitative preparation and analysis of RNA and DNA in samples as small as one cell. BMC Biotechnology, vol. 5(2), p. 1-13, 2005.*
Bengtsson, M. et al., "Gene expression profiling in single cells from the pancreatic islets of Langerhans reveals lognormal distribution of mRNA levels," Genome Res. 15 (2005) 1388-1392.
Blake, W. et al., "Noise in eukaryotic gene expression," Nature 422 (Apr. 10, 2003) 633-637.
Boom, R. et al, "Rapid and Simple Method for Purification of Nucleic Acids," Journal o Clinical Microbiology 28:3 (Mar. 1990) 495-503.
Bustin, S., "Absolute quantification of mRNA using real-time reverse transcription polymerase chain reaction assays," Journal of Molecular Endocrinology 25 (2000) 169-193.
Cai, L. et al., "Stochastic protein expression in individual cells at the single molecule level," Nature 440 (Mar. 16, 2006) 358-362.
Chomczynski, P. et al., "Single-Step Method of RNA Isolation by Acid Guanidinium Thiocyanate-Phenol-Chloroform Extraction," Analytical Biochemistry 162 (1987) 156-159.
Elowitz, M., "Stochastic Gene Expression in a Single Cell," Science 297 (Aug. 16, 2002) 1183-1186.
Freeman, W. et al., "Quantitative RT-PCR: Pitfalls and Potential," BioTechniques 26:1 (1999) 112-125.
Ginsberg, S., "RNA amplification strategies for small sample populations," Methods 37 (2005) 229-237.
Kawaski, E., "Microarrays and the Gene Expression Profile of a Single Cell," Ann N.Y. Acad. Sci. 1020 (2004) 92-100.
Levsky, J. et al., "Single-Cell Gene Expression," Science 297 (Aug. 2, 2002) 836-840.
Liss, B., "Improved quantitative real-time RT-PCR for expression profiling of individual cells," Nucleic Acids Research 30:17 (2002) e89, 9 pages.
Nolan, T. et al., "Quantification of mRNA using real-time RT-PCR," Nature Protocols 1:3 (2006) 1559-1582.
Olofsson, C. et al., "Fast Insulin Secretion reflects exocytosis of docked granules in mouse pancreatic B-cells," Eur J Physiol 444 (2002) 43-51.
Peixoto, A. et al., "Quantification of Multiple Gene Expression in Individual Cells," Genome Research 14 (2004) 193-1947.
Raj, A. et al., "Stochastic mRNA Synthesis in Mammalian Cells," PLOS Biology 4:10 (Oct. 2006) e309 1707-1719.
Ross, I. et al., "Transcrition of individual genes in eukaryotic cells occurs randomly and infrequently," Immunology and Cell Biology 72 (1994) 177-185.
Schuit, F. et al., "Glucose stimulates proinsulin biosynthesis by a dose-dependent recruitment of pancreatic beta cells," Proc. Natl. Acad. Sci. USA 85 (Jun. 1988) 3865-3869.
Stahlberg, A. et al., "Properties of the Reverse Transcription Reaction in mRNA Quantification," Clinical Chemistry 50:3 (2004) 509-515.

(Continued)

*Primary Examiner* — Prabha Chunduru
(74) *Attorney, Agent, or Firm* — Dinsmore & Shohl, LLP

(57) ABSTRACT

The present invention is directed to a method for performing an RT-PCR for amplifying a target RNA comprising the steps of a) lysis of a cellular sample which is supposed to contain the target RNA with a lysis buffer comprising between 0.2 M and 1 M guanidine thiocyanate, b) diluting the sample to an extend such that guanidine thiocyanate is present in a concentration of about 30 to 50 mM, c) reverse transcribing in the presence of a mixture of first strand cDNA synthesis primers, the mixture consisting of oligo dT primers and random primers, and d) subjecting the sample to multiple cycles of a thermocycling protocol and monitoring amplification of the first strand cDNA in real time.

12 Claims, 7 Drawing Sheets

(56) References Cited

OTHER PUBLICATIONS

Stahlberg, A. et al., "Comparison of Reverse Transcriptases in Gene Expression Analysis," Clinical Chemistry 50:9 (2004) 1678-1680.

Tang, F. et al., "MicroRNA expression profiling of single whole embryonic stem cells," Nucleic Acids Research 34:2 (2006) e9 7 pages.

Can Roy, N. et al., "Accurate normalization of real-time quantitative RT-PCR data by geometric averaging of multiple internal control genes," Genome Biology 3:7 (2002) 34.1-34.11.

Verma, M., Use of Ammonium Sulfate Precipitation and Guanidine Isothiocyanate Lysis to Isolate Lambda DNA, Bio Techniques 7 (1989) 230-232.

Weintraub, H., "Formation of stable transcription complexes as assayed by analysis of individual templates," Proc. Natl. Acad. Sci. USA 85 (Aug. 1988) 5819-5823.

Yamada, O. et al., "A new method for extracting DNA or RNA for polymerase chain reaction," Journal of Virological Method 24 (1990) 203-210.

Yamaguchi, M. et al., "Effect of Different Laboratory Guanidinium-Phenol-Chloroform RNA Extraction of S260/A280 and on Accuracy of mRNA Quantitation by Reverse Transcriptase-PCR," PCR Methods and Applications 1 (1992) 286-290.

\* cited by examiner

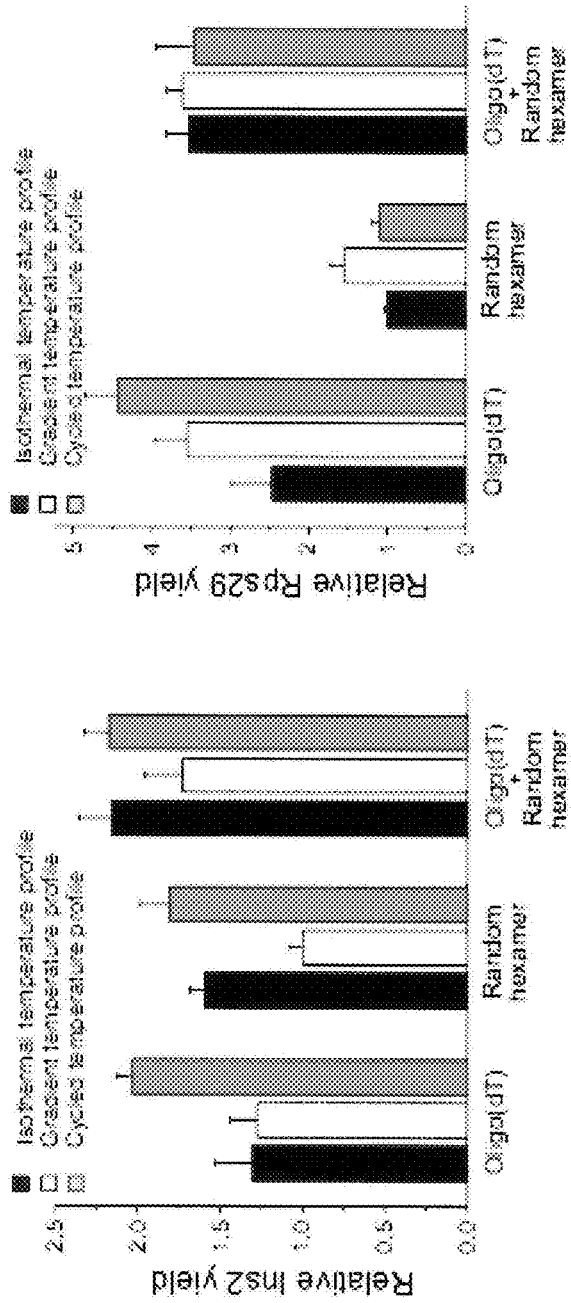
Fig. 3 B (con't.)

SINGLE CELL MRNA QUANTIFICATION WITH REAL-TIME RT-PCR

RELATED APPLICATIONS

This application is a continuation of PCT/EP2008/003451 filed Apr. 29, 2008 and claims priority to EP 07008961.0 filed May 3, 2007.

FIELD OF THE INVENTION

The present invention provides a method for mRNA measurements in single mammalian cells. Using quantitative PCR, together with optimized procedures for cell collection, lysis and reverse transcription, the method allows the study of transcript numbers, distributions, correlations, and gene induction at the single cell level.

BACKGROUND

Cells in a population are in many aspects unique in their characteristics, even in a seemingly homogenous culture or tissue. Gene expression levels show large cell-cell variations, due to external (extrinsic) and internal (intrinsic) sources of factors. Likewise, when exposed to identical stimuli, cells often behave stochastically. This means that data obtained from a population of cells can not be assumed to reflect the behavior of the individual cell. It has been suggested that cells can respond to stimuli by bursts in transcriptional activity and operate as a binary switch; that is in an all-or-none fashion.

To determine whether two transcripts are expressed in a parallel (expression high at the same time) or anti-parallel (one is high when the other is low), transcription analysis at the level of the individual cell is required. When groups of cells are analyzed at the same time, important information is lost. For example, it is not possible to discriminate between a small change in gene transcription occurring in every cell as opposed to major changes in only a few cells. Furthermore, cell heterogeneity is tissues makes cell-type specific analysis difficult. These issues are resolved by measurements in individual cells.

A typical eukaryotic cell contains about 25 pg of RNA of which less than 2% is mRNA. This corresponds to a few hundred thousands of transcripts of the ~10,000 genes that are expressed in each cell at any particular point in time. Imaging techniques such as multiplex fluorescent in situ-hybridization (FISH) can monitor gene transcriptional activity spatially within a single cell by labelling of specific mRNAs and may be applied to living cells to provide temporally resolved glimpses of the complexity of the transcription machinery. Protein levels in single cells have been measured quantitatively in bacteria and yeast using fluorescent reporter proteins. For a complete transcriptome analysis of a single cell, microarrays, preceded by non-specific amplification of cDNA, are used. The most widespread method for single cell mRNA analysis is reverse transcription polymerase chain reaction (RT-PCR), and the related quantitative real-time RT-PCR (qRT-PCR). This technique offers superior sensitivity, accuracy, and dynamic range compared to alternative methods for mRNA measurements. The number of transcripts that can be readily analyzed in the single cell is small, but pre-amplification of cDNA vastly increases this number.

However, the protocols for single cell analysis that exist in the art so far are useful only with respect to the detection of abundantly expressed targets. These methods do not provide the sensitivity required to detect target mRNAs that are expressed as a comparatively low level.

SUMMARY OF THE INVENTION

Thus, in a first aspect, the, present invention is directed to a method for performing an RT-PCR for amplifying a target RNA comprising the steps of
 a) lysis of a biological sample consisting of only a few cells which is supposed to contain said target RNA with a lysis buffer comprising between 0.05 M and 1 M Chaotropic agent
 b) diluting said sample to an extend such that Chaotropic agent is present during step c) in a concentration of about 10 to 60 mM
 c) without any intermediate purification step reverse transcribing said target RNA in the presence of a mixture of first strand cDNA synthesis primers, said mixture consisting of primers hybridizing to a poly-A sequence and/or random primers
 d) subjecting said sample to multiple cycles of a thermocycling protocol and monitoring amplification of said first strand cDNA in real time.

This method is typically applicable if the sample comprises only a limited number of cells, i.e. not more that 100 cells, and preferably less than 10 cells. In particular, the method is applicable even if the sample comprises only a single cell.

Preferably, step a) is performed for at least 5 minutes at a temperature between about 75° C. to 85° C.

Also preferably, said chaotropic agent is guanidine thiocyanate. Alternatively said chaotropic agent may be come selected from a group consisting of Guanine Hydrochloride, Potassium Cyanate and Ammonium Sulphate.

In one important embodiment, said biological sample consist of not more than 100 cells or preferably not more than 10 cells. In one specific important embodiment, said biological sample is a single cell.

Preferably, the lysis buffer comprises between about 0.2 and 0.5 M Chaotropic agent.

Also preferably, during step c), i.e. during the reverse transcriptase reaction, Chaotropic agent is present in a concentration of about 10-60 mM, more preferably between 30 and 50 mM and most preferably about 40 mM.

Optionally, the reverse transcriptase reaction may be-performed in the presence of 0.5 to 2% NP 40 (nonyl phenoxylpolyethoxylethanol).

The incubation of step a) at a temperature between about 75° C. to 85° C. may in some cases be performed in the presence of proteinase K at concentrations as described below.

Optionally, the sample is frozen at temperatures between about −20° C. and −80° C. between steps a) and b).

According to the present invention it is highly preferable, if said mixture of cDNA synthesis primers comprises both: primers hybridizing to a poly-A sequence as well as random primers.

The random primer is usually a random hexamer primer. The primers hybridizing to a poly-A sequence are usually oligo-dT primers or Oligo-dU primers. In a preferred embodiment, said primers hybridizing to a poly-A sequence and random primers are present in equal amounts. In another preferred embodiment, which is compatible with the above mentioned one, said primers hybridizing to a poly-A sequence and random primers are present in concentrations between 1 µM and 5 µM each. Highly preferred are concentrations of about 2.5 mM each.

In a very specific embodiment suitable for analysis of multicellular biological samples, the method according the present invention comprises the steps of a) lysis of a biological sample which is supposed to contain said target RNA with a lysis buffer comprising between 0.2 M and 1 M guanidine thiocyanate by means of incubation for at least 5 minutes at a temperature between about 55° C. to 85° C. in the presence or absence of Proteinase K incubation for about 2 to 10 minutes at 95° C.

freezing said sample at −25° C.

b) diluting said sample to an extent such that guanidine thiocyanate is present in a concentration of about 20 to 60 mM.

c) reverse transcribing in the presence of a mixture of first strand cDNA synthesis primers, said mixture consisting of random sequence primers and primers hybridizing to a poly-A sequence.

d) subjecting said sample to multiple cycles of a thermocycling protocol and monitoring amplification of said first strand cDNA in real time.

In another very specific embodiment suitable for analyis of single cells, the method according the present invention comprises the steps of a) lysis of a single cell which is supposed to contain said target RNA with a lysis buffer comprising between 0.2 M and 1 M guanidine thiocyanate by means of incubation for at least 10 minutes at a temperature between about 75° C. to 85° C. in the presence or absence of Proteinase K freezing said sample at −75° C. to −80° C.

b) diluting said sample to an extend such that guanidine thiocyanate is present in a concentration of about 30 to 50 mM.

c) reverse transcribing in the presence of a mixture of first strand cDNA synthesis primers, said mixture consisting of primers hybridizing to a poly-A sequence and random primers d) subjecting said sample to multiple cycles of a thermocycling protocol and monitoring amplification of said first strand cDNA in real time.

DETAILED DESCRIPTION OF THE INVENTION

The method according to the present invention permits gene expression profiling in only a few cells and even in a single cell. Species of mRNA in single cells or a few cells are quantified by qRT-PCR. At a cell population scale, gene expression levels are commonly normalized to reference genes [15]. The stochastic nature of single cells makes this approach invalid, leaving absolute quantification as the best option to compare transcript levels within and between cells. In order to improve the experimental protocols to optimize cell lysis and mRNA accessibility, the mRNA yield in the reverse transcription reaction and quality assessment were thus systematically analyzed. The method was demonstrated on single cells from the pancreatic islets of Langerhans in mouse, revealing transcript copy numbers, co-regulation of gene expression, and distribution of transcript expression levels.

Figure 1:
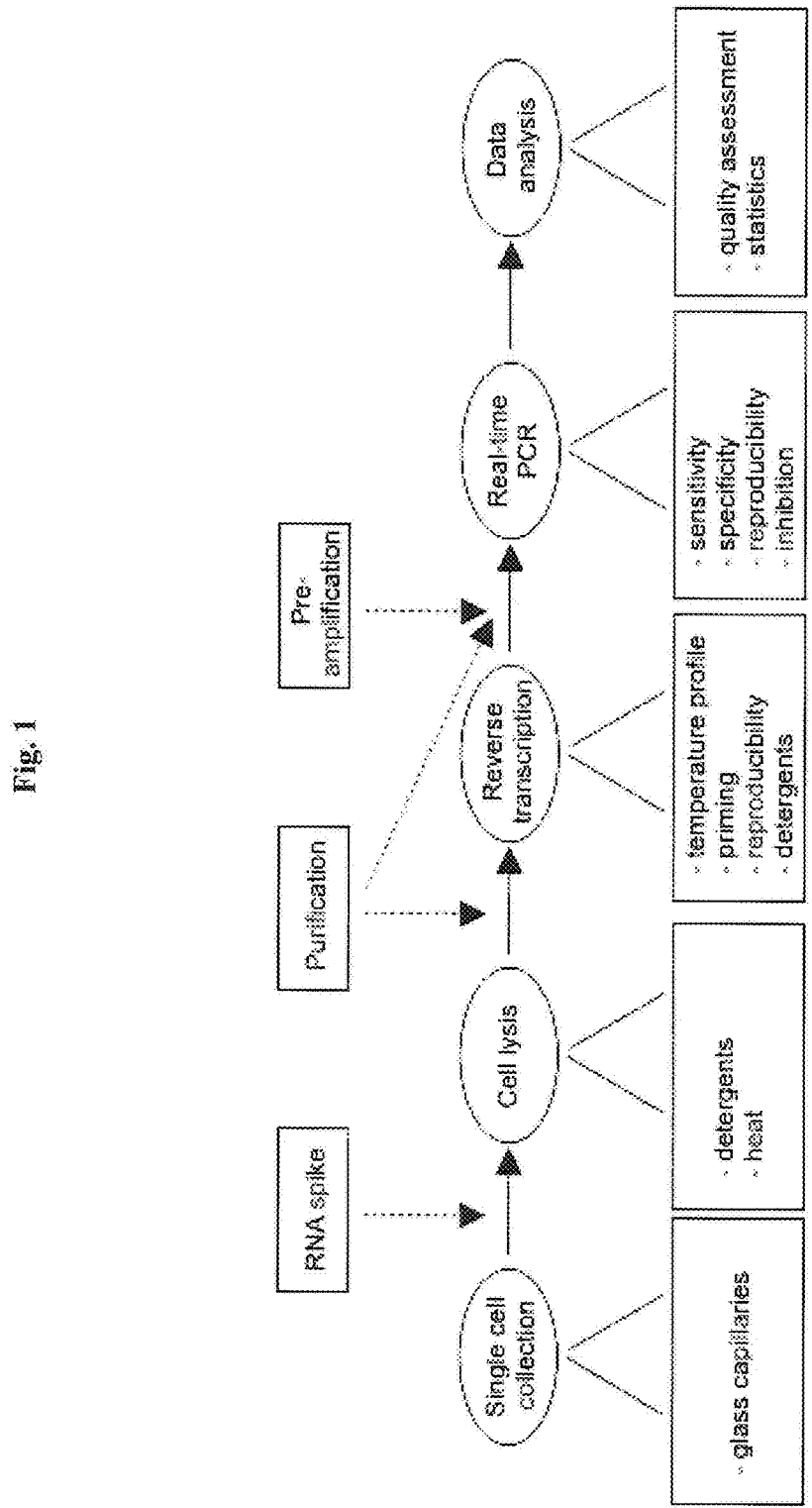
FIG. 1: Overview of single cell gene expression profiling using qRT-PCR. The alternatives and important issues for each step in the procedure that were addressed in this study are shown in boxes. Optional steps are shown in dotted arrows.

Dispersed cells were collected with a glass capillary, emptied in lysis buffer and analyzed with qRT-PCR. FIG. 1 outlines the experimental procedure. For quality assessment, an artificial RNA molecule based on the cyclophilin E (Ppie) gene was generated by in vitro transcription. An equal amount of Ppie RNA was added together with lysis buffer to all reaction tubes before the single cell was deposited into the tube. The RNA could reduce the adsorption of the cell itself or single cell mRNAs to surfaces. Samples with deviant cycle of threshold (Ct) values for the Ppie RNA spike may result from degradation by RNases. These samples were re-analyzed and, if the problem remained, excluded from further analysis. The presence of inhibitors may reduce the cDNA yield.

Figure 2:
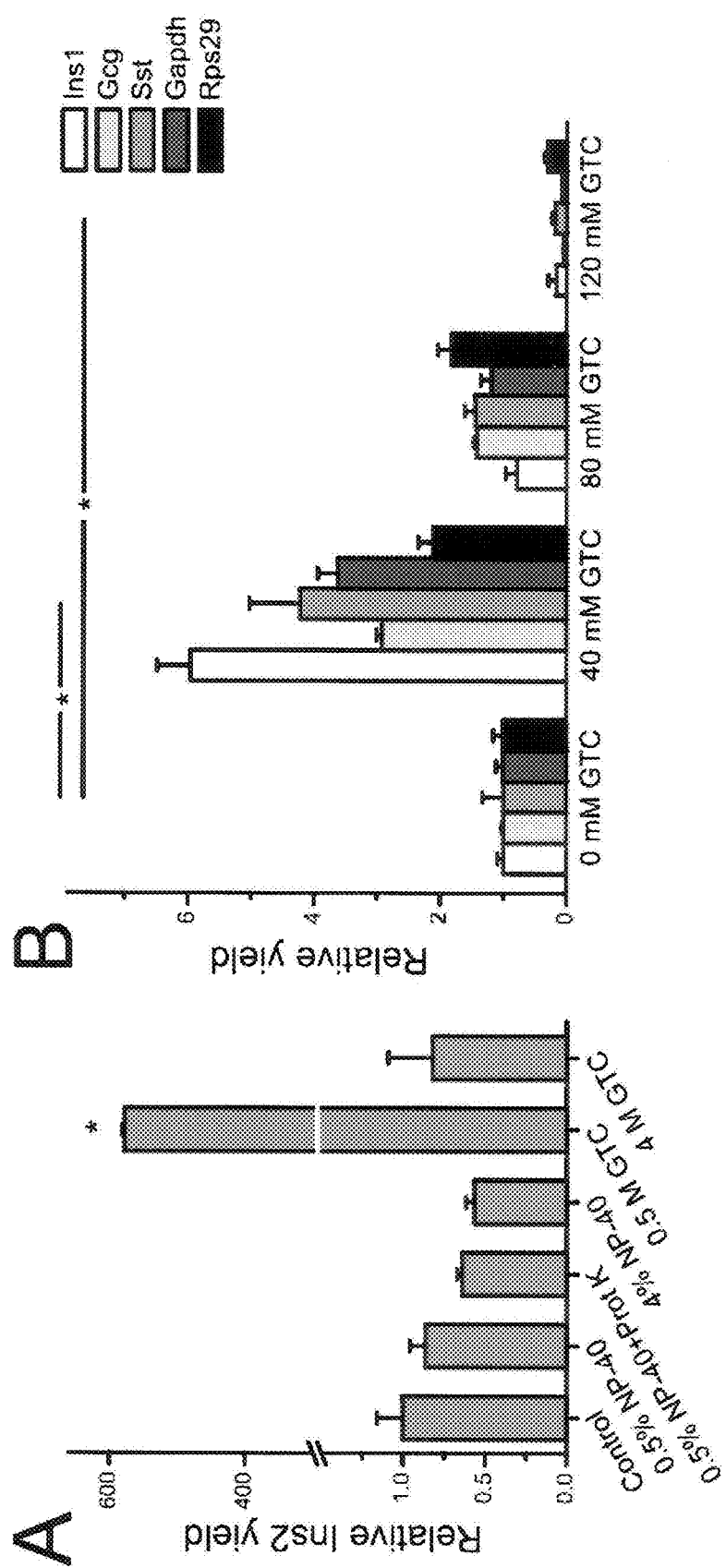
FIG. 2: Evaluation of lysis buffers. (A) Determination of lysis efficiency. Each bar indicate relative yield of Ins2 using a single pancreatic islet (~2000 cells) as starting material. Each islet was treated with indicated concentrations of either NP-40, with and without proteinase K (Prot K) treatment, or guanidine thiocyanate (GTC). Only lysis with 0.5 M GTC had a significant effect compared to control conditions ($p<0.001$, n=3). (B) Effect of lysis buffers on RT reaction yield. Identical amounts of purified islet total RNA was used as starting material. Relative yields of five genes were analysed: Ins1, Gcg, Sst, Gapdh and Rps29. Increasing concentrations of guanidine thiocyanate was added to the RT reaction. There is a significant difference for all genes between control and both 40 mM and 120 mM ($p<0.05$) but not 80 mM. Values are mean±SEM for 3 separate experiments.

The purpose of the lysis buffer is to make the mRNA accessible for the RT enzyme. Two detergents were chosen for this task, a weak, non-chaotropic (Igepal CA-630, a.k.a. NP-40) and a strong, chaotropic (guanidine thiocyanate, GTC). The lysis efficiency and potential influence on the downstream RT reaction was evaluated. Five different lysis conditions were evaluated in terms of their ability to lyse one pancreatic islet (FIG. 2A). NP-40 had no effect compared to control (water) when used at concentrations of 0.5% or 4%. Proteinase K had no effect when added in the presence of 0.5% NP-40. GTC based lysis buffer provided efficient lysis of the islet using a concentration of 0.5 M and increased the RNA yield 600-fold; an effect that was strongly diminished at 4 M.

Then, the lysis buffers with respect to their effect on the RT-reaction were compared. Low concentrations (0.1%) of NP-40, regardless of addition of proteinase K, did not have an effect compared to control conditions. However, when used at a concentration of 1%, NP-40 resulted in small but significant improvement of RT-efficiency. In FIG. 2B, three concentrations of GTC (40 mM, 80 mM, and 120 mM) were tested on five genes. The reaction efficiency was significantly improved (2-6 fold) for all tested genes using 40 mM GTC. By contrast, 80 mM GTC had no effect whereas 120 mM GTC was in fact inhibitory. The addition of 0.5-1-5% 2-mercapto ethanol did not improve the yield of the RT reaction either alone or in concert with GTC (data not shown). Formation of correct PCR-products was confirmed by agarose gel electrophoresis. Of the tested detergents, GTC was chosen due to superior lysis ability and positive effect on the RT reaction at the concentration of 40 mM.

Figure 3:
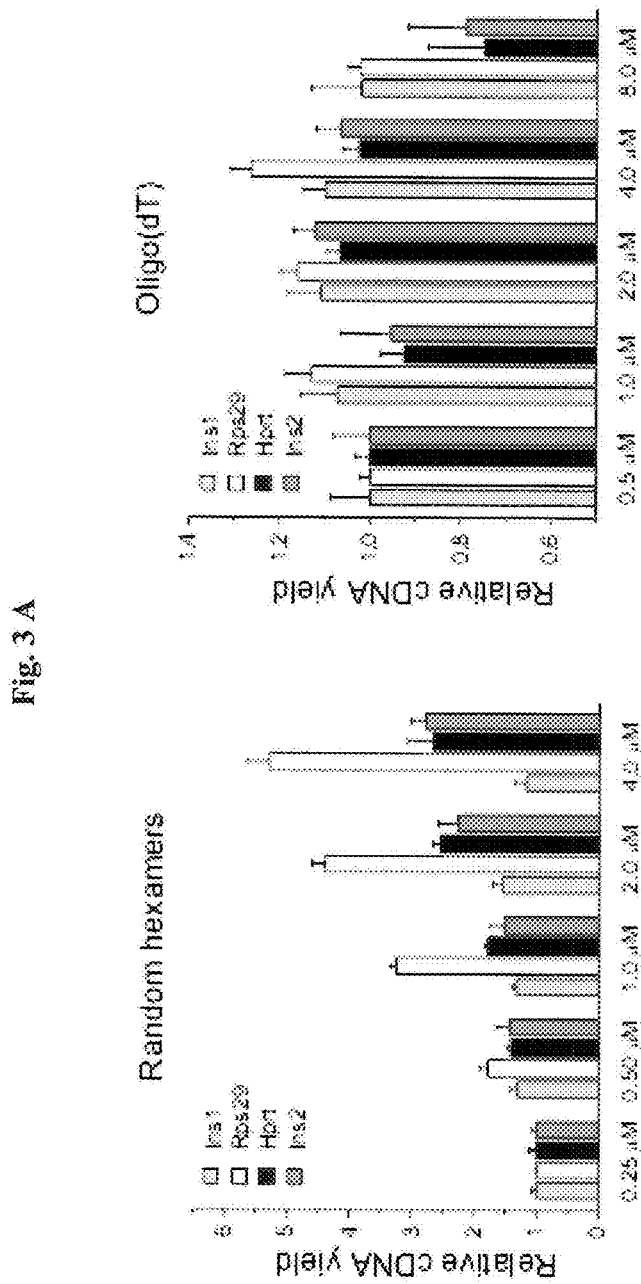
FIG. 3: Optimization of the RT reaction. Four genes were measured: Ins1, Ins2, Rps29 and Hprt. (A) Determination of optimal RT primer concentration using either oligo(dT) or random hexamers. (B) Comparison of RT priming strategies and temperature profiles. Identical amounts of purified total RNA from MIN6 cells was used as starting material. Relative RT reaction yields are shown for various primer combinations. 2.0 µM of either oligo(dT) or random hexamers or both was used. Temperature profiles used are isothermal (black bars), gradient (white bars) and cycled (grey bars). Values are mean±SEM for 3 separate experiments.
Figure 3:
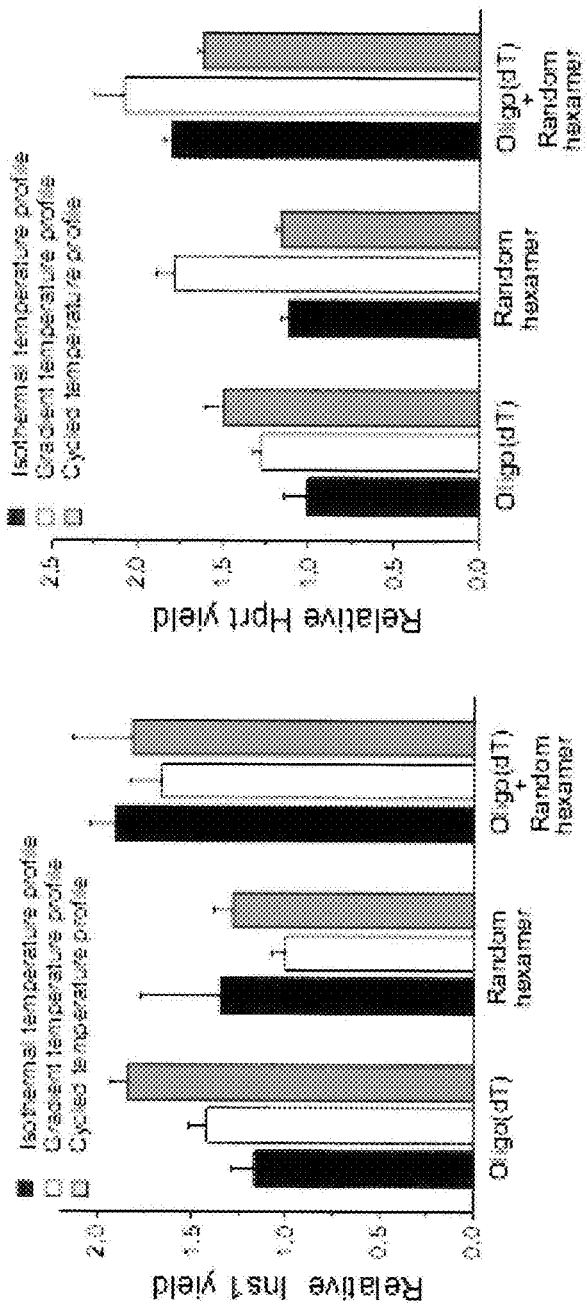

Proper quantification of rare transcripts requires efficient cDNA generation by reverse transcription (RT). In FIG. 3, priming of the RT reaction by random hexamers and oligo(dT) nucleotides were investigated for four genes: insulin 1 (Ins1), insulin 2 (Ins2), ribosomal protein S29 (Rps29) and hypoxanthine guanine phosphoribosyl transferase (Hprt). The effect of RT primer concentration was analyzed (FIG. 3A). The RT efficiency generally increased with increasing primer concentration, although there were some differences between the measured genes. 2.0 µM of either oligo(dT) or random hexamer priming result in a high cDNA yield. In FIG. 3B, the effect of combining RT-primers and temperature profiles was tested. Three different temperature profiles (isothermal, gradient and cycled temperature profiles) were evaluated in combination with random hexamer and oligo(dT) priming strategies. The combination of both priming methods were in all cases superior or equal to the single best priming method used. It could be hypothesized that the initiation of the RT reaction, at which stage the RT primer anneals to its target mRNA molecule, is critical. A gradually increasing temperature (gradient) would allow low melting point RT primers to anneal to its target, while strong secondary structures denature in the later stages of the incubation. A cycled temperature profile was also tested which was recently reported to increase the cDNA yield for quantification of miRNA [14]. However, there was no significant difference in yield or reproducibility between the tested temperature profiles. There was 2-5-fold difference between worst and best primer/temperature combination. One can conclude that a combination of 2.0 µM oligo(dT) and 2.0 µM random hexamers maximizes the yield of the RT reaction.

In addition to oligo(dT) and random hexamer priming, RT-priming with gene-specific primers (GSP) was tested. For some genes, concentration dependent formation of non-specific products in the downstream PCR was observed. This effect was pronounced when using a mixture of different GSPs. To determine whether this was an effect on the RT or the PCR, GSPs were added directly to the PCR. A total concentration >0.4 µM GSPs in the PCR resulted in formation of erroneous PCR products. However, dilution of cDNA reverse transcribed with GSP did only partly remove the formation of unspecific products. Thus, high concentrations of GSPs affect both RT and PCR reactions negatively.

Figure 4:
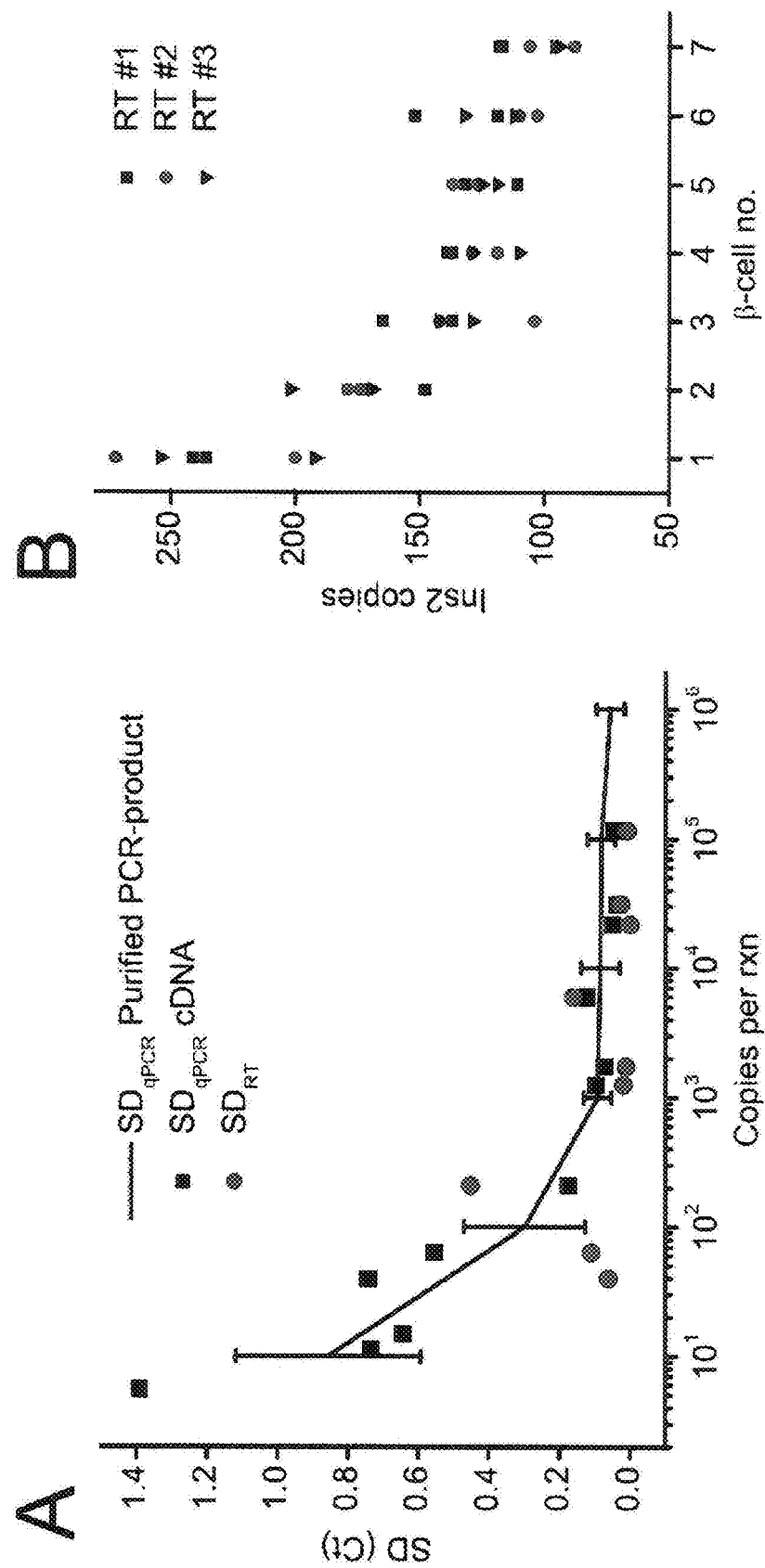
FIG. 4: Technical reproducibility of RT and qPCR. (A) Dilutions of purified total islet RNA, equivalent with the amount found in a single cell, were run in triplicate RT and triplicate qPCR reactions. Standard deviation (SD) of measurements on three genes (Ins1, Ins2 and Gcg) is shown, with the contribution from qPCR (black squares) and RT (red circles). The SD of qPCR triplicate reactions based on predetermined amounts of purified PCR product of Ins1, Ins2, Gcg, Rps29 and Hprt are shown as reference (solid black line). The variability between these five assays is shown as (SD) error bars. (B) Single β-cells were measured with triplicate RT and duplicate qPCR reactions to visualize the variability in single cell mRNA measurements. The Ins2 copy number refers to numbers of molecules in the RT reaction. Approximately 3% of the original cell was analyzed in each reaction.

The technical reproducibility of RT and qPCR is presented in FIG. 4A. The reproducibility of the RT and qPCR reaction, represented here by standard deviation in Ct values (SDRT and SDqPCR respectively), are shown for a range of different initial copy numbers In addition, SDqPCR was calculated from dilution of purified PCR-product. There is no difference between SDqPCR from cDNA or PCR-product, indicating that the technical reproducibility is intrinsic of the qPCR reaction itself and not due to interfering factors from upstream reactions. All reactions are highly reproducible down to ~1000 copies (approx. Ct 28-30), and acceptable down to ~100 copies. At <100 copies the variability in the RT and PCR reactions is a considerable obstacle for accurate quantification of mRNA. FIG. 4B shows the technical variation in context of the biological, cell-to-cell variation. Single cells from the islets of Langerhans in mice were collected and analyzed in triplicate RT reactions and duplicate qPCR reactions. The technical variation is on par with the one observed in FIG. 4A. Though the cell-to-cell variation for the collected β-cells was relatively small, the technical variation is smaller, and allows absolute quantification with sufficient accuracy in the range of 100-200 molecules.

For analysis of gene expression profiling in single cells from the endocrine pancreas of the mouse, Ins1, Ins2, glucagon (Gcg), Rps29. and chromogranin B (Chgb) were measured in 158 cells collected from four incubations with different glucose concentrations (3, 6, 10 and 20 mM). Islets of Langerhans in the pancreas are heterogeneous and contains 1000-3000 cells comprising at least four endocrine cell types, where insulin-secreting β-cells and glucagon-producing α-cells are the most abundant [18]. Based on presence of insulin or glucagon transcripts, these cells were distinguished as β-cells (126 cells, 83%), α-cells (25 cells, 16%) or unknown (1 cell, 0.7%). Six samples were negative for all measured genes and they were categorized as technical failures (96% success rate). For all genes, lognormal distribution was confirmed and the geometric means were calculated as shown in the following table:

TABLE 1

Statistical parameters describing gene expression in single pancreatic α- and β- cells

| Gene | N[1] | Geometric mean | log$_{10}$ Geometric mean (SD) | Shapiro Wilk P-value[2] |
|---|---|---|---|---|
| Ins2 | 124 | 8900 | 3.9 (0.5) | 0.53 |
| Ins1 | 100 | 3100 | 3.5 (0.5) | 0.57 |
| Gcg | 25 | 19000 | 4.3 (0.3) | 0.25 |
| Rps29 | 102 | 230 | 2.4 (0.3) | 0.98 |
| Chgb | 59 | 82 | 1.9 (0.5) | 0.67 |

[1]N is the number of cells expressing the tested gene. $N_{tot}$ = 158.
[2]A high Shapiro-Wilk value reflects a good fit, in this case to the lognormal distribution.

The data allowed for a correlation of expression levels in the individual cells as it is shown in the following table. The Pearson correlation factor for Ins 1 and Inst was 0.59, which indicates single cell correlation.

TABLE 2

Pearson correlation coefficients of expression levels in single cells

|  | Ins2 | Ins1 | Gcg | Rps29 | Chgb |
|---|---|---|---|---|---|
| Ins2 | 1 | | | | |
| Ins1 | 0.59 | 1 | | | |

TABLE 2-continued

Pearson correlation coefficients of expression levels in single cells

|       | Ins2 | Ins1 | Gcg   | Rps29 | Chgb |
|-------|------|------|-------|-------|------|
| Gcg   | N.A. | N.A. | 1     |       |      |
| Rps29 | 0.18 | 0.19 | −0.25 | 1     |      |
| Chgb  | 0.08 | 0.14 | 0.06  | 0.31  | 1    |

Figure 5:
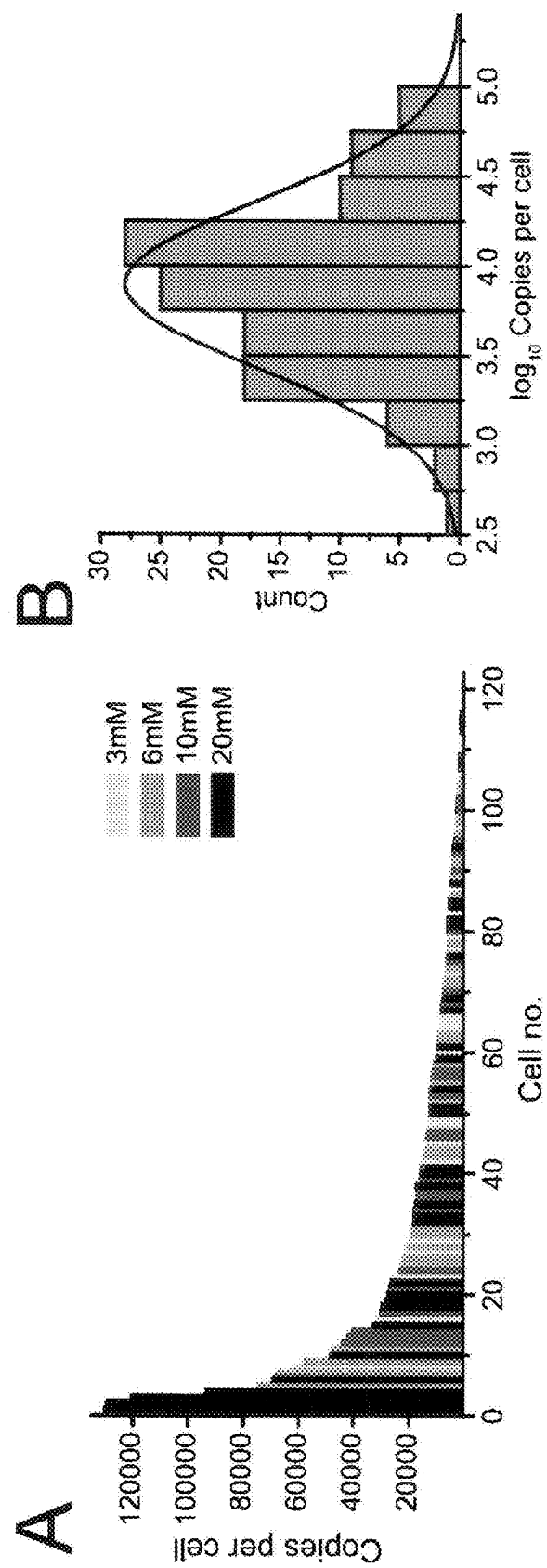
FIG. 5: Ins2 transcripts quantified in 126 β-cells from the Islets of Langerhans. (A) The expression level of Ins2 for each β-cell, incubated in 3, 6, 10 or 20 mM glucose, as indicated. (B) The histogram shows that the expression levels of Ins2 are lognormally distributed. Transcript levels are mean-centered for the four glucose concentrations.

All populations of cells showed a large heterogeneity in transcript levels. For example, of the 35 β-cells incubated in 20 mM glucose, the four cells with highest expression account for 50% of the total Ins2 mRNA (FIG. 5A). As indicated in studies on pooled cells, increasing glucose concentration had a stimulating effect on Ins1, Ins2 and Chgb and a slight negative effect on Gcg. A stronger effect of glucose on insulin and glucagon in the cells with high expression levels was observed. Out of the 14 cells with the highest Ins2 levels (top 20%), 11 were incubated in 20 mM glucose while three were in 3 mM glucose. Corresponding ratio between 20 and 3 mM glucose incubations were 12 to 1 for Ins1 and 0 to 2 for Gcg. Expression levels were lognormally distributed for all genes at every glucose concentration.

Like any investigation of small and sensitive mechanisms, single cell transcription profiling requires careful preparations and highly optimized reaction conditions for a successful outcome. The results of the disclosed study allows definition of optimal conditions that will enable to experimenter to avoid pitfalls by using the right reagents at the ideal concentrations.

While the effect on lysis is indisputable and expected—i.e. GTC was superior in lysing the islet—its effect on the RT reactions is more complex. While high concentrations (>100 mM) severely disturb the reaction, low concentrations (~40 mM) has a favorable effect on the RT yield. GTC is a strong chaotropic detergent. The positive effect of GTC may act by reducing secondary structures, thus allowing greater access to the mRNA for primers and reverse transcriptase.

According to the present invention, it is preferred to use a combination of random hexamer and oligo(dT) in the RT reaction irrespective of the temperature profile used. In agreement with previous findings [16], the results are highly gene dependent and thorough optimizations is needed for highest possible RT efficiency. Priming of RT by gene-specific primers (GSP) is occasionally used in mRNA quantification. There are two explanations to the formation of unspecific PCR products of cDNA primed with GSPs: Firstly, the total primer concentration in the cDNA used in the PCR can reach levels approaching that of the PCR primers. This could interfere with the amplification and generate unspecific products. Secondly, GSPs bind largely unspecific to the mRNA [16]. Thus, the resulting cDNA will be similar to that of random hexamer priming, but with the GSP primer in the 3' end.

In five measurements of a cell with 100 copies of a particular transcript, the results will span approximately 10-40 copies per reaction (corresponding to 50-200 copies per cell). This spread is mostly due to variation in the qPCR, and it is in line with the biological variation between cells. Duplicate or triplicate qPCR reactions will provide increased accuracy, and allow quantification of lower levels.

In addition, the reproducibility of results obtained with single cell preparations in NP40 in milliQ water was compared with preparations in 0.3 M GTC by means of calculating the standard deviations of 6 RT-PCR reactions each. For this experiment, each cell was divided into three RT replicates and each of these were later divided into PCR duplicates. Hence, the standard deviation (SD) was based on six samples.

The results showed that the standard deviation was is substantially lower (and therefore reproducibility higher) for cells prepared in 0.3 M GTC.

Summarizing, according to the method of the present invention, the cells are deposited in the strong detergent guanidine thiocyanate, optionally together with an RNA spike for quality assessment. 30 to 5.0 mM concentration of guanidine thiocyanate is a potent reverse transcription reaction enhancer. A combination of random hexamer and oligo (dT) priming ensures a high cDNA yield.

EXAMPLES

Example 1

Preparation and Culture of Cells

Pancreatic islets were prepared from healthy female National Maritime Research Institute (NMRI) mice aged 3-4 months (Bomholtgaard, Ry, Denmark) and fed a normal diet ad libitum. The mice were sacrificed by cervical dislocation, and pancreatic islets were isolated by collagenase P digestion (Roche, Basel, Switzerland) followed by manual collection of islets. All experimental procedures involving animals were approved by the ethical committee of Lund University. To prepare dispersed single cells the collected islets were gently shaken at low extracellular $Ca^{2+}$ concentration to dissolve the structure of the islet [21]. Dispersed cells were plated on plastic 35 mm Petri dishes (Nunc, Roskilde, Denmark) in RPMI 1640 medium (SVA, Uppsala, Sweden) supplemented with 10% FCS, 100 U $mL^{-1}$ penicillin, and 10 $\mu g m L^{-1}$ streptomycin (all from Invitrogen, Carlsbad, Calif., USA) in the presence of various concentrations of glucose (Sigma-Aldrich, St. Louis, Mo., USA). The cells were maintained in culture 18-24 hours for the glucose stimulation experiment and for 2-6 hours for other experiments.

MIN6 cells were cultured in 5 mM glucose as previously described [2].

Example 2

Single Cell Collection

Attached dispersed cells were washed twice with a buffer containing 138 mM NaCl, 5.6 mM KCl, 1.2 mM $MgCl_2$, 2.6 mM $CaCl_2$, 5 mM HEPES (pH 7.4 with NaOH) and 3-20 mM glucose (same glucose concentration as in culture) to remove dead and loose debris for cell collection with patch-clamp pipettes. The dish, containing adhered cells and approximately 1 mL buffer, was mounted in a standard inverted light-microscope (Zeiss Axiovert 135, Oberkochen, Germany). Borosilicate glass capillaries (Hilgenberg GmbH, Malsfeld, Germany) with outer diameter of 1.6 mm and wall thickness of 0.16 mm were pulled to pipettes using a patch-clamp pipette puller (Heka PIPS, Lambrecht, Germany). The diameter of the tip was approximately 10 μm on average, substantially wider than standard patch-clamp pipettes and large enough to allow passage of an intact cell. The glass pipette was mounted on a hydraulic micromanipulator (Narishige, Tokyo, Japan) on the microscope. By controlling the pressure inside the pipette it was possible to collect intact or nearly intact cells with minimum volume of extracellular solution.

Example 3

Lysis and Purification

Islet lysis: Single pancreatic islets of roughly the same size were placed in 10 μl of various lysis buffers. The detergents Nonidet P-40 (NP-40, a.k.a. Igepal CA-630, Sigma-Aldrich) and guanidine thiocyanate (GTC, Sigma-Aldrich) were used. Samples were incubated at 60° C. or 80° C. for 15 minutes (60° C. for samples containing 0.4 mg/ml proteinase K (Invitrogen)) followed by 5 min incubation at 95° C. and frozen at −25° C. for subsequent analysis. Samples were diluted 1:20 prior reverse transcription to minimize possible inhibitory effects.

Single cell lysis: In single cell experiments, the glass pipettes were emptied in 0.2 ml plastic tubes containing 2 µl of lysis solution. The emptying required a custom-made device, consisting of a tube holder lined up with a coarse micromanipulator on which the pipette was mounted. The glass pipette was carefully flushed with lysis buffer a few times to make sure the cell entered the tube. In most cases, the tip of the pipette was gently broken in the tube thereby facilitating the flushing of the pipette. Tubes were then immediately placed on a heating block with heated lid at 80° C. for 5 minutes. Several compositions of the lysis buffers, containing either NP-40 or GTC, were evaluated. Unless indicated otherwise, the detergents were diluted in mQ purified water, but occasionally in a buffer containing 50 mM Tris-Cl pH 8.0, 140 mM NaCl, 1.5 mM $MgCl_2$ (all Sigma) was used. Following the heat treatment, the samples were immediately frozen on dry ice (−78° C.) and stored at −80° C. for subsequent reverse transcription.

Total RNA extraction: Some optimization experiments were performed with total RNA from larger cell populations. Total RNA was purified with GenElute Mammalian Total RNA Kit (Sigma-Aldrich) and concentrations were measured with a NanoDrop ND-1000 spectrophotometer (Nanodrop Technologies, Wilmington, Del., USA).

Example 4

In Vitro Transcription

To generate an artificial RNA control we used the T7 RNA Polymerase in vitro transcription system (Takara, Shiga, Japan). A PCR assay for cyclophilin E (Ppie) was used as template for the in vitro transcription. First, the Ppie PCR product was generated using the same setup as for the real-time PCR assays, except that all fluorophores were excluded. The PCR product was purified using PCR purification kit (Qiagen, Hilden, Germany) and then amplified again in a new PCR reaction with an extended forward PCR primer where the promoter sequence for T7 RNA Polymerase was added. The final PCR product was purified as above and used in the in vitro transcription reaction, according to the manufacturer's instruction. The 20 µL reaction mix contained: 40 mM Tris-HCl (pH 8.0), 8 mM $MgCl_2$, 2 mM spermidine, 5 mM dithiothreitol (all Takara), 2 mM NTP (Invitrogen), 20 U RNaseOut (Invitrogen) and ~40 ng template DNA. The reaction was incubated at 42° C. for 1 h.

Example 5

Reverse Transcription

The reverse transcriptase SuperScript III (Invitrogen) was used throughout the study [17]. 6.5 µL containing total RNA or lysed single cells, 0.5 mM dNTP (Sigma-Aldrich), 2.5 µM oligo(dT) (Invitrogen), 2.5 µM random hexamers (Invitrogen) and if indicated 0.5 µM of each gene specific primer (identical to reverse PCR primer, Invitrogen or MWG-Biotech, Ebersberg, Germany) were incubated at 65° C. for 5 min. Various combinations of RT-primers were used in this work and alternative strategies are described in the results. We then added 50 mM Tris-HCl (pH 8.3), 75 mM KCl, 3 mM $MgCl_2$, 5 mM dithiothreitol, 20 U RNaseOut and 100 U SuperScript III (all Invitrogen) to final volume of 10 µL. Final reaction concentrations are shown. The temperature profiles used were: isothermal, 25° C. for 5 min; 50° C. for 45 min; gradient, 25-40° C. for 1 min/° C., 41-65° C. for 5 min/° C.; cycled, 50 cycles at 25° C. for 30 sec, 50° C. for 30 sec and 55° C. for 5 sec. All reactions were terminated at 70° C. for 15 min. For calculations of standard deviation of the RT-qPCR reaction, triplicate RT and triplicate qPCR reactions on diluted purified total mouse islet RNA was used [16].

Example 6

Quantitative Real-time PCR

Real-time PCR measurements were carried out on the ABI PRISM 7900HT Sequence Detection System (Applied Biosystems, Foster City, Calif., USA) in 10 och 20 µL reactions. The PCR mix contained: 10 mM Tris (pH 8.3), 50 mM KCl 3 mM $MgCl2$, 0.3 mM dNTP, 1 U JumpStart Taq polymerase (all Sigma-Aldrich), 0.5×SYBR Green I (Invitrogen), 1×Reference Dye (Sigma-Aldrich) and 400 nM of each primer (MWG-Biotech). Formation of expected PCR products was confirmed by agarose gel electrophoresis (2%) for all assays, and melting curve analysis for all samples. Real-time PCR data analysis was performed as described, and PCR efficiencies were calculated from dilution series of purified PCR-products (QIAquick PCR purification kit, Qiagen) [12,19]. Absolute copy numbers of purified PCR products were calculated using the following molar absorptivity values (in Moles-1 cm-1): dAMP, 15200; dTMP, 8400; dGMP, 12010; dCMP, 7050. A260 was measured with the NanoDrop ND-1000 spectrophotometer.

Abbreviations Used:

Ct, Cycle of threshold; GSP, gene specific RT-primer; qRT-PCR, quantitative reverse transcription polymerase chain reaction; RT, reverse transcription; SD, standard deviation

What is claimed is:

1. A method for performing an RT-PCR for amplifying a target RNA comprising the steps of
   lysing a biological sample which contains the target RNA with a lysis buffer comprising between 0.05 M and 1 M of a chaotropic agent,
   diluting the buffer comprising the target RNA to an extent such that said chaotropic agent is present for a subsequent reverse transcription step in a concentration of 10 to 60 mM,
   without any intermediate purification step, reverse transcribing said target RNA in the presence of a mixture of first strand cDNA synthesis primers into a first strand cDNA, said mixture consisting of primers hybridizing to a poly-A sequence and/or random primers, and
   subjecting the transcription mixture comprising the transcribed RNA to multiple cycles of a thermocycling protocol and monitoring amplification of said first strand cDNA in real time,
   wherein said biological sample consists of not more than 10 cells and the chaotropic agent is guanidine thiocyanate.

2. The method according to claim 1 wherein said lysis buffer comprises between 0.2 and 0.5 M chaotropic agent.

3. The method according to claim 1 wherein during the reverse transcription step, said chaotropic agent is present at a concentration between 30 to 50 mM.

4. The method according to claim 1 wherein the reverse transcription step is performed in the presence of 0.5 to 2% NP 40 (nonyl phenoxylpolyethoxylethanol).

5. The method according to claim 1 wherein the lysis step is performed for at least 5 minutes at a temperature about 75° C. to 85° C.

6. The method according to claim 5 wherein the lysis step is performed further in the presence of proteinase K.

7. The method according to claim 1 wherein between the lysis and the dilution steps, the sample is frozen at temperatures between about −20° C. and −80° C.

8. The method according to claim 1 wherein said mixture of cDNA synthesis comprises primers hybridizing to a poly-A sequence and random primers.

9. The method according to claim 8, wherein primers hybridizing to a poly-A sequence and random primers are present in essentially equal molar amounts.

10. The method according to claim 8 wherein said primers hybridizing to a poly-A sequence and random primers are present in concentrations between 1 μM each.

11. The method according to claim 9 wherein said primers hybridizing to a poly-A sequence and random primers are present in concentrations of about 2.5 μM each.

12. The method of claim 1, wherein the biological sample is a single cell.

* * * * *